US008907074B2

United States Patent
Ryu et al.

(10) Patent No.: US 8,907,074 B2
(45) Date of Patent: Dec. 9, 2014

(54) **LATICIFEROUS TISSUE-SPECIFIC SRPP PROMOTER FROM *HEVEA BRASILIENSIS* AND USES THEREOF**

(75) Inventors: Beung Tae Ryu, Daejeon (KR); Jeong Sheop Shin, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/878,397

(22) PCT Filed: Oct. 10, 2011

(86) PCT No.: PCT/KR2011/007492
§ 371 (c)(1),
(2), (4) Date: Apr. 8, 2013

(87) PCT Pub. No.: WO2012/047076
PCT Pub. Date: Apr. 12, 2012

(65) Prior Publication Data
US 2013/0212742 A1    Aug. 15, 2013

(30) Foreign Application Priority Data
Oct. 8, 2010    (KR) .................. 10-2010-0098075

(51) Int. Cl.
*C12N 15/82*     (2006.01)
*C12N 15/87*     (2006.01)
*A01H 5/00*      (2006.01)
*C12N 15/00*     (2006.01)
*C12N 15/113*    (2010.01)
*C07K 14/415*    (2006.01)

(52) U.S. Cl.
CPC .......... *C12N 15/8223* (2013.01); *C12N 15/113* (2013.01); *C07K 14/415* (2013.01)
USPC ....... 536/24.1; 800/278; 800/295; 435/320.1; 435/468

(58) Field of Classification Search
None
See application file for complete search history.

(56) References Cited

U.S. PATENT DOCUMENTS 5,294,593 A * 3/1994 Khan ........................... 504/100
2003/0119098 A1   6/2003 Hallahan

FOREIGN PATENT DOCUMENTS

KR    10-0781059 B1    11/2007
KR    10-0789274 B1    12/2007

OTHER PUBLICATIONS

Agrawal et al, Latex: a model for understanding mechanisms, ecology, and evolution of plant defense against herbivory, Annu. Rev. Ecol. Evol. Syst. (2009) 40:311-31.*
Xiankun et al, Cloning and functional analysis of the gene promoter of small rubber particle protein (SRPP) in *Hevea brasiliensis*, Chinese Agricultural Science Bulletin (2009) 25:241-247.*
Oh et al, Isolation, characterization, and functional analysis of a novel cDNA clone encoding a small rubber particle protein from *Hevea brasiliensis*, J. of Biol. Chem. (1999) 24:17132-17138.*
Jefferson et al., 1987, Plant Mol. Biol. Rep. 5:387-405.
Krens, F.A. et al., 1982, Nature 296, 72-74.
Negrutiu I. et al., Jun. 1987, Plant Mol. Biol. 8, 363-373.
Shillito R.D. et al., 1985 Bio/Technol. 3, 1099-1102.
Crossway A. et al., 1986, Mol. Gen. Genet. 202, 179-185.
Klein T.M. et al., 1987, Nature 327, 70.
Xiao-Wen Fei, "In vitro Transient Expression System of Latex C-serum was used for Analysis of Hevein Promoter in Response to Abscisic Acid in *Hevea brasiliensis*", Journal of Integrative Plant Biology, 2008, V. 50, 338-344.
J. Leclercq, "The green fluorescent protein as an efficient selection marker for *Agrobacterium tumefaciens*-mediated transformation in *Hevea brasiliensis* (Mull. Arg)", Plant Cell Reports, Published online Mar. 20, 2010, V. 29, 513-522.
Guilan Li . "Functional analysis of an *Aspergillus ficuum* phytase gene in *Saccharomyces cerevisiae* and its root-specific, secretory expression in transgenic soybean plants", Biotechnol Letter, 2009, V. 21, 1297-1202.
Clay Carter , "The nectary-specific pattern of expression of the tobacco Nectarin I promoter is regulated by multiple promoter elements", Plant Molecular Biology, 2002, V. 51, 451-457.

* cited by examiner

*Primary Examiner* — Cathy Kingdon Worley
*Assistant Examiner* — Mykola Kovalenko
(74) *Attorney, Agent, or Firm* — The PL Law Group, PLLC

(57) ABSTRACT

A laticiferous tissue-specific SRPP (small rubber particle-associated protein) promoter derived from *Hevea brasiliensis*, consists of nucleotide sequence of SEQ ID NO: 1. A recombinant plant expression vector includes the promoter. A plant is transformed with the recombinant plant expression vector and seed of the transformed plant is obtained. A method for laticiferous tissue-specific expression of a foreign gene in a transformed plant includes performing recombination of a foreign gene into the recombinant plant expression vector. The transformed plant produced by the method shows laticiferous tissue-specific expression of a foreign gene.

9 Claims, 5 Drawing Sheets

FIG. 1

Pre-Immune        SRPP Antibody

FIG. 2

1) *Hevea* genomic DNA extraction (leaf)

2) Digestion of Genomic DNA with Taq I and Primer design

3) Self ligation and PCR

4) TA vector cloning and Sequencing

Wild Type    SRPPpro::GUS

FIG. 7

Wild Type    SRPPpro::GUS

FIG. 8

Wild Type      SRPPpro::*GUS*

SEQUENCE LISTING

<160> NUMBER OF SEQ ID NOS: 3

<210> SEQ ID NO 1
<211> LENGTH: 660
<212> TYPE: DNA
<213> ORGANISM: Hevea brasiliensis

<400> SEQUENCE: 1

```
cgaattcagt gtttaagaac taaaagtttt cttccctgat ccagaactct catttttctt      60
ttcatcaacc atggctctga taccatgtaa aaaaactaag aaattttgga ataagaattc     120
ttatctttat tgccccagaa ataaaatata tatataaaaa aattacagct aacaaatagg     180
tccctaatca agctaaacta ccaaaattgt atcaaagtca tacaacaaaa ggtaaaaaca     240
gatatgcaca caaaaattcc taaacaaatg ccctaaataa atacaaaata agtgacagct     300
aacagctgca tttccaataa ttaatttaac taataaaatt tataatctta aaaataattt     360
taatattatt gaattaaaat ttataaataa aattaacact gttaaaatta aaagaaaatt     420
attaagattt gaattttttaa gcggttattt aattttgaaa aacaaggcta acttttttt     480 tatataattt actaaaaaat tcatgaatga aaaaaaaatc cataagtaaa cttaccccat     540
acgggttatg cacgctaaac caataaaaca gaaacacgtt tatacactcg ttttcatttt     600
ccatctataa atagagagat ttgtttttag ttttaaacca taatcagttg atagcttcca     660
```

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2

```
tggtccatta aaacctggtg tcga                                             24
```

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3

```
gatatgtcct tggcataaag gtaga                                            25
```

LATICIFEROUS TISSUE-SPECIFIC SRPP PROMOTER FROM *HEVEA BRASILIENSIS* AND USES THEREOF

CROSS REFERENCE TO RELATED APPLICATIONS AND CLAIM OF PRIORITY

This patent application is a National Phase application under 35 U.S.C. §371 of International Application No. PCT/KR2011/007492, filed Oct. 10, 2011, which claims priority to Korean Patent Application No. 10-2010-0098075 filed Oct. 8, 2010, entire contents of which are incorporated herein by reference.

BACKGROUND

1. Technical Field

The present invention relates to laticiferous tissue-specific SRPP promoter from *Hevea brasiliensis* and uses thereof. More specifically, it relates to laticiferous tissue-specific SRPP (small rubber particle-associated protein) promoter derived from *Hevea brasiliensis* which consists of nucleotide sequence of SEQ ID NO: 1, a recombinant plant expression vector including the promoter, a plant transformed with the recombinant plant expression vector and seed of the transformed plant, a method for laticiferous tissue-specific expression of a foreign gene in a transformed plant including performing recombination of a foreign gene into the recombinant plant expression vector, and a transformed plant produced by the method which shows laticiferous tissue-specific expression of a foreign gene, and seed of the transformed plant.

2. Background Art

Para rubber tree (*Hevea brasiliensis*) generally known as a rubber tree is a plant belonging to family *Euphorbiaceae*, and it is economically the most important tree among the genus *Hevea*. Para rubber tree can produce a large amount of latex, which is a main raw material of natural rubber, and is currently known as almost only natural rubber resource which can be industrially used. Ninety percent or more of natural rubber is produced in Southeast Asia region including Malaysia, Indonesia, Thailand, and Myanmar. In Korea, almost 200,000 tons or more of natural rubber are consumed every year, while all of them depend on import.

Rubber biosynthesis in a rubber tree occurs on surface of rubber particles that are floating in latex, which is a cytoplasm of lactifer of a rubber tree. It is known that several RPPs (rubber particle-associated protein) bind to rubber particles. Among them, SRPP (small rubber particle-associated protein) is known as a protein which binds to small rubber particles with diameter of 10 μm or less. However, it is still not clearly determined based on histoanatomical analysis whether or not SRPP is indeed expressed only in latex tissues.

Protein synthesis is initiated by a transcription process by which genetic information encoded in DNA is delivered to mRNA. Specifically, transcription is initiated by binding of a RNA polymerase to a promoter located at an upstream region of a gene. Every promoter has a consensus sequence on a constant location relative to transcription initiation point, and it is known to be important for recognition of promoter and binding by RNA polymerase. The promoter is one of the important factors which determine the production efficiency of a recombinant protein.

Conventionally used CaMV35S promoter from cauliflower mosaic virus is a promoter exhibiting excellent expression efficiency in any tissue of a dicot plant, and therefore it can be most advantageously used for gene expression in plant. However, this promoter is not suitable for tissue-specific expression of a certain gene by transformation. Thus, studies are needed for developing a promoter for tissue-specific expression which can eliminate unnecessary expression as much as possible in undesired tissues.

Inventors of the present invention produced an antibody against SRPP recombinant protein, and by performing immunostaining analysis, tried to determine whether or not expression of SRPP gene derived from *Hevea brasiliensis* occurs in laticiferous tissue-specific manner.

In Korean Patent No. 10-0789274, a novel promoter derived from *Corynebacterium glutamicum* is disclosed. In Korean Patent No. 10-0781059, a method of preparing a transformed plant for guard cell-specific expression of a target protein by using an environmental stress-inducible promoter derived from *Arabidopsis* is disclosed.

SUMMARY

The present invention was devised under the circumstances described above, and the inventors of the present invention completed the present invention through the processes as follows: laticiferous tissue-specific expression of SRPP (small rubber particle-associated protein) protein from a para rubber tree (*Hevea brasiliensis*) is confirmed by histoanatomical method, nucleotide sequence of SRPP promoter is defined, a transformation vector (pBI101-SRPPpro::GUS) in which Marker gene (GUS) is linked to SRPP promoter is prepared, Russian dandelion as a model plant which has laticiferous tissue and is suitable for transformation is transformed with the vector, and induction of laticiferous tissue-specific expression of GUS protein by SRPP promoter is determined.

To solve the problems described above, the present invention provides SRPP (small rubber particle-associated protein) promoter derived from a para rubber tree (*Hevea brasiliensis*), which consists of nucleotide sequence of SEQ ID NO: 1.

The present invention also provides a recombinant plant expression vector including the promoter.

The present invention also provides a plant transformed with the recombinant plant expression vector and seed of the transformed plant.

The present invention also provides a method for laticiferous tissue-specific expression of a foreign gene in a transformed plant including performing recombination of a foreign gene into the recombinant plant expression vector.

The present invention also provides a transformed plant produced by the method which shows laticiferous tissue-specific expression of a foreign gene in a transformed plant, and seed of the transformed plant.

By using the SRPP promoter derived from a para rubber tree (*Hevea brasiliensis*) of the present invention, a transformed plant which specifically expresses a foreign gene in a laticiferous tissue can be obtained, and thus it is expected to contribute to control of biosynthetic pathway of natural rubber and increase or decrease of production amount in a plant.

DETAILED DESCRIPTION

In order to achieve the purpose of the present invention, the present invention provides SRPP (small rubber particle-associated protein) promoter derived from a para rubber tree (*Hevea brasiliensis*), which consists of nucleotide sequence of SEQ ID NO: 1. Preferably, the SRPP promoter can express a certain gene in a laticiferous tissue-specific manner.

Compared to CaMV35S promoter from cauliflower mosaic virus, that has been widely used, can express an incorporated gene in entire tissues, the laticiferous tissue-specific SRPP promoter according to the present invention can be used for laticiferous tissue-specific expression of a gene incorporated to the transformed plant.

Further, variants of the promoter sequence are also within the scope of the present invention. Specifically, the variants indicate a nucleotide sequence which has functional characteristics similar to the base sequence of SEQ ID: 1. Specifically, the promoter gene may include a nucleotide sequence with at least 70%, preferably at least 80%, more preferably at least 90%, and most preferably at least 95% sequence homology with the nucleotide sequences of SEQ ID NO: 1.

The "sequence homology %" for a certain polynucleotide is determined by comparing two nucleotide sequences that are optimally arranged with a region to be compared. In this regard, a part of the polynucleotide sequence in a region to be compared may include an addition or a deletion (i.e., a gap) compared to a reference sequence (without any addition or deletion) relative to the optimized arrangement of the two sequences.

Also provided by the present invention is a recombinant plant expression vector including the SRPP promoter. Preferably, the recombinant plant expression vector may be constructed by operably linking a target gene which encodes a target protein to a downstream of the SRPP promoter. As used herein, the term "operably linked" indicates an expression cassette component which functions as a unit for expressing heterogeneous protein. For example, a promoter operably linked to a heterogeneous DNA encoding a protein promotes production of functional mRNA which corresponds to the heterogeneous DNA.

The laticiferous tissue-specific expression vector of the present invention can be used as a transient expression vector which allows transient expression of a foreign gene in a plant and also as a plant expression vector which allows permanent expression of a foreign gene in a plant.

A binary vector which can be used for the present invention can be any binary vector including RB (right border) and LB (left border) of T-DNA which can transform a plant when it is present with Ti plasmid of *A. tumefaciens*. Preferably, pBI101 (Cat#: 6018-1, Clontech, USA), pBIN19 (Genbank Deposit No. U09365), pBI121, pCAMBIA and the like, which are often used by a skilled person in the pertinent art, are used.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in a form of a sense or antisense, that are not found in natural state of cell. In addition, a recombinant cell can express a gene that is found in natural state, provided that said gene is modified and re-introduced into the cell by an artificial means.

The term "vector" is used herein to refer DNA fragment(s) and nucleotide molecules that are delivered to a cell. Vector can replicate DNA and be independently reproduced in a host cell. The terms "delivery system" and "vector" are often interchangeably used. The term "expression vector" means a recombinant DNA molecule including a desired coding sequence and other appropriate nucleotide sequences that are essential for the expression of the operably-linked coding sequence in a specific host organism. The promoter, enhancer, termination signal and polyadenylation signal which can be used in eukaryotic cells are well known in the art.

A preferred example of plant expression vector is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the gene of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be appropriately transformed.

Expression vector may include at least one selective marker. Said selective marker is a nucleotide sequence having a property that can make a target gene get selected by a common chemical method. Examples include all genes that are useful for distinguishing transformed cells from non-transformed cells. Specific examples include a gene resistant to herbicide such as glyphosate and phosphinothricin, and a gene resistant to antibiotics such as kanamycin, G418, bleomycin, hygromycin, and chloramphenicol, but not limited thereto.

In the above-described recombinant vector of the present invention, any kind of a typical terminator can be used. Example includes, nopalin synthase (NOS), rice α-amylase RAmy1A terminator, phaseoline terminator, and a terminator for Octopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the context of the present invention.

Also provided by the present invention is a plant transformed with the recombinant plant expression vector and seed of the transformed plant.

Transformation of a plant means any method which can transfer DNA to a plant. Such transformation is not necessarily required to have a period for regeneration and/or tissue culture. Transformation of a plant is now generally carried out not only for a dicot plant but also for a monocot plant. In principle, any method for transformation can be used for introducing a heterologous DNA of the present invention to a progenitor cell. Transformation can be carried out according to any method selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. According to the present method, *Agrobacterium* mediated DNA transfer is preferred. In particular, so-called binary vector technique as disclosed in EP A 120 516 and U.S. Pat. No. 4,940, 838 can be preferably adopted for the present invention.

The "plant cell" that is used for the plant transformation according to the present invention can be any plant cell. The plant cell can be a cultured cell, a cultured tissue, a cultured organ, or a whole plant, preferably a cultured cell, a cultured tissue or a cultured organ, and more preferably any form of a cultured cell.

The "plant tissue" includes either differentiated or undifferentiated plant tissue, including fruit, stem, leaf, pollen, seed, cancerous tissue and cell lines having various shape that are used for culture, i.e., single cell, protoplast, bud and callus tissue, but not limited thereto. Plant tissue can be in planta or in a state of organ culture, tissue culture or cell culture.

Also provided by the present invention a method for laticiferous tissue-specific expression of a foreign gene in a transformed plant including performing recombination of a foreign gene into the recombinant plant expression vector and transforming a plant with the recombinant plant expression vector. The foreign gene described above may encode a protein which is selected from a group consisting of a rubber polymerase, an enzyme relating to biosynthesis of rubber, interleukin, interferon, platelet-derived growth factor, hemoglobin, elastin, collagen, insulin, fibroblast growth factor, human growth factor, human serum albumin, erythropoietin, and the like, but not specifically limited thereto.

The foreign gene may be any gene desired to be expressed in a laticiferous tissue of plant, and in the laticiferous tissue-specific expression vector of the present invention, it is present behind the promoter, and if necessary, it may be expressed after fusion with a reporter gene. The method for transforming a plant with the recombinant laticiferous tissue-specific expression vector can be carried out as described above.

Also provided by the present invention is a transformed plant produced by the method, which shows laticiferous tissue-specific expression of a foreign gene in a transformed plant, and seed of the transformed plant. Preferably, the plant may be a dicot plant, but not limited thereto.

The dicot plant may be Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae or Umbelliferae (Apiaceae), but not limited thereto.

Herein below, the present invention is explained in greater detail in view of the Examples. However, it is evident that the following Examples are given only for exemplification of the present invention and by no means the present invention is limited to the following Examples.

EXAMPLES

Example 1

Preparation of Antibody Against SRPP Protein

In order to see laticiferous tissue-specific expression of SRPP gene, an antibody against SRPP recombinant protein (expressed in *E. coli*) was prepared.

Example 2

Histoanatomical Immunostaining Analysis of SRPP Protein on Cross-Section of Petiole of *Hevea brasiliensis*

Tissue Fixation and Embedding for Immunohistochemical Localization

The tissue blocks were prepared from a leaf petiole using blazer and were immersed immediately in fixation buffer (4% (v/v) paraformaldehyde in phosphate buffered saline (PBS)) to avoid latex outflow. After fixing overnight, the tissue blocks were rinsed with PBS. Then the blocks were embedded quickly in compound (Tissue-Tek OCT; Sakura Finetechnical Co. Ltd., Tokyo, Japan), and snap-frozen in liquid nitrogen. Then 40-μm-thick sections were cut and kept at 20° C. in a cryostat (CM-1850; Leica Microsystems).

Immunohistochemical Localization

All subsequent steps were conducted at room temperature. After removal of OCT compound with PBS, sections were blocked in PBS containing 10% horse serum (Gibco, Auckland, New Zealand) for 20 min. Then 50 μl of each mouse primary antibody diluted to concentration 10 μg/ml in fresh PBS, containing 10% horse serum and 0.1% Triton X-100, was added to the sections with subsequent incubation for 6 h. The sections were then rinsed three times for 10 min each with PBS. Then 50 μl of secondary antibody conjugated with alkaline phosphatase diluted to concentration 10 μg/ml in fresh PBS, containing 10% horse serum and 0.1% Triton X-100, was added to the sections and incubated for another 4 h. The sections were again rinsed three times for 10 min each with PBS, and then colored by adding p-nitrophenol, substrate of the phosphatase (Planta Vol. 230, Number 1, 215-225, DOI: 10.1007/s00425-009-0936-0).

Figure 1:
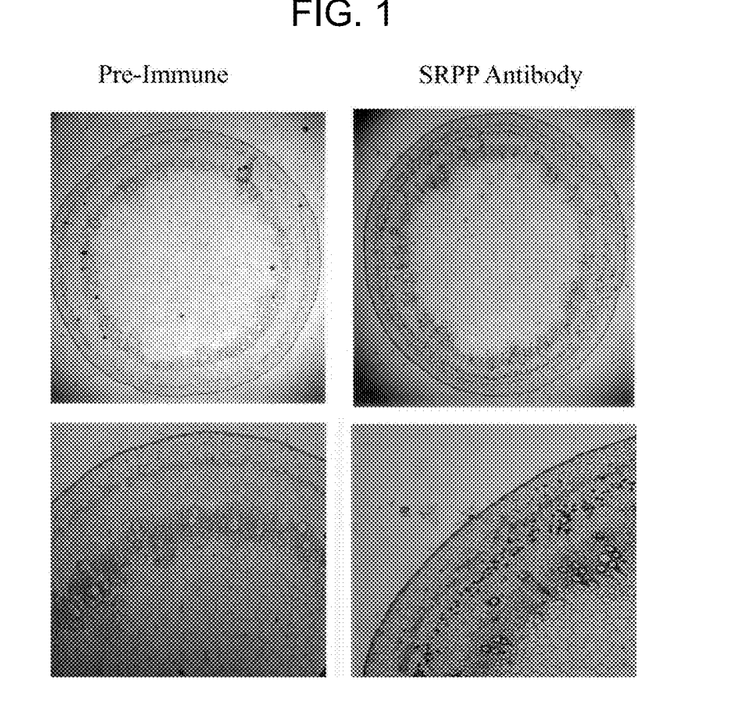
FIG. 1 shows a result of identifying expression location of SRPP protein in a leaf petiole of a para rubber tree based on immunohistoanatomical analysis.

As a result, it was confirmed that expression of SRPP protein occurs in laticiferous tissue-specific manner (FIG. 1).

Example 3

Isolation of SRPP Gene Promoter from Leaves of *Hevea brasiliensis*

Figure 2:
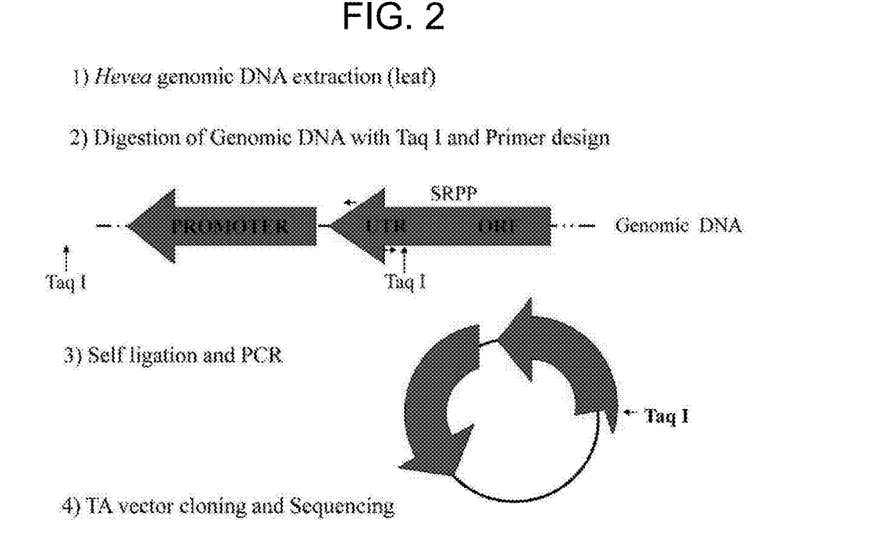
FIG. 2 is a schematic drawing showing the process of isolating SRPP promoter from the genomic DNA which has been extracted from leaves of a para rubber tree.

From the leaf tissues of *Hevea brasiliensis*, genomic DNA was extracted according to a common method. The extracted genomic DNA was then treated with TaqI for digestion, and the digested genomic DNA fragments were subjected to a treatment with TaqI followed by self-ligation. After that, a primer was constructed in both directions at Taq I site in SRPP 5'-UTR P 5'-UTR (non-translated region) and used for PCR reaction as follows (5'-TGGTCCATTAAAACCTGGT-GTCGA-3' (SEQ ID NO: 2) and 5'-GATATGTCCTTG-GCATAAAGGTAGA-3' (SEQ ID NO: 3)). Thereafter, the promoter region isolated by PCR was sequenced (FIG. 2).

Example 4

Construction of Transformation Vector Including GUS Gene Bound to SRPP Promoter

Figure 3:
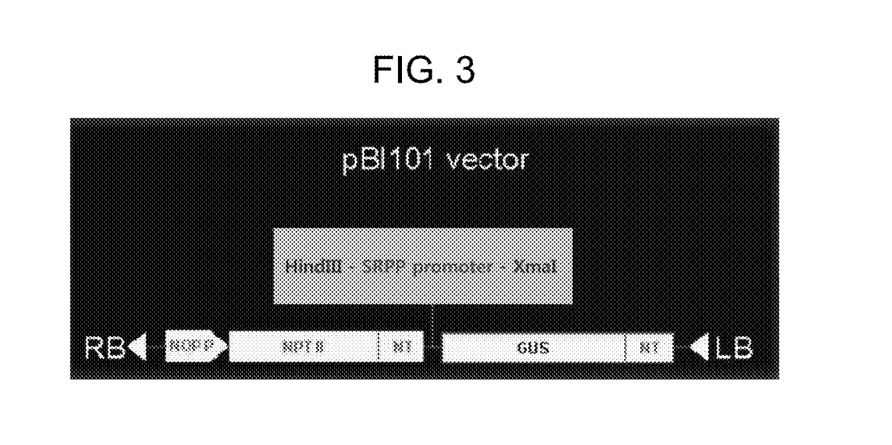
FIG. 3 is a schematic drawing showing the transformation vector which has been constructed for promoter-GUS analysis.

In order to induce GUS expression, i.e., a marker gene, by inserting SRPP promoter to HindIII/XmaI of pBI101 vector, the recombinant vector (pBI101-SRPPpromoter::GUS) was constructed (FIG. 3). The isolated SRPP promoter was inserted between HindIII and XmaI of pBI101 to construct a recombinant vector (pBI101-SRPPpromoter::GUS) for inducing the expression of GUS gene.

Example 5

Transformation of Laticiferous Model Plant (Russian Dandelion)

Figure 4:
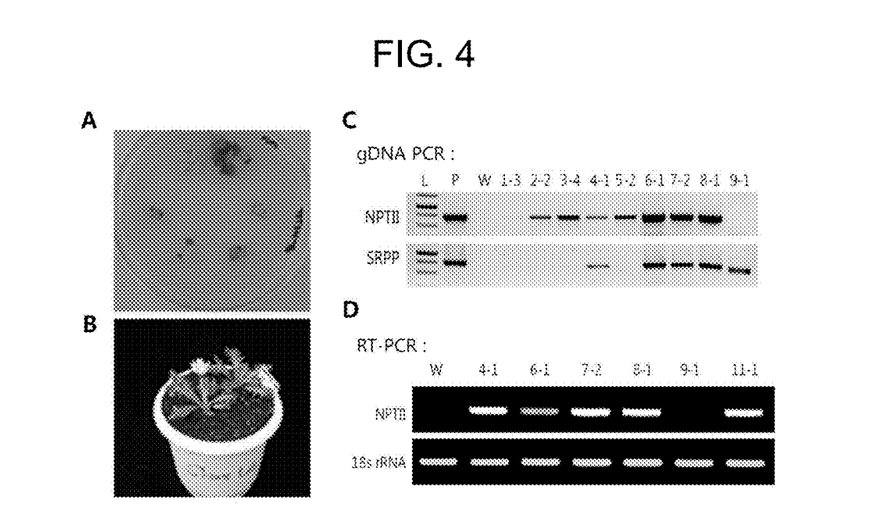
FIG. 4 includes photographs demonstrating the process (A) through (D) of transforming Russian dandelion having laticiferous tissue with pBI101-SRPP promoter::GUS.

Since *Hevea brasiliensis* from which SRPP has been isolated is not easily transformed and also, as being a forest tree, requires several years to give results, Russian dandelion as a model laticiferous plant which can be relatively easily transformed and has short growth period was used for transformation. Specifically, the pBI101-SRPPpromoter::GUS vector was introduced to *Agrobacterium* strain GV3101, and transformation of Russian dandelion was performed by the method described by Bae et. al. (2005, Plant Cell, Tissue and Organ Culture 80: 51-57). The SRPPpro::GUS transformant was selected on a selection medium and grown for 2 to 3 months in a soil medium (FIGS. 4A and B: (A) Young shoots transformed in callus of leaf fragment are visible in a kanamycin selection medium. (B) Transformed Russian dandelion was transferred to a soil medium and grown for 2 to 3 months). Thereafter, genomic DNA and total RNA were extracted and transformation was again determined based on PCR and RT-PCR analysis, respectively (FIGS. 4C and D: (C) Genomic DNA was extracted and the transformants were subjected to a first determination. (D) Total RNA was extracted, and based on expression of NPTII (kanamycin) gene, final five lines of transformed Russian dandelion were selected).

Example 6

Tissue-Specific Expression of GUS Gene in Transformed Russian Dandelion

Figure 5:
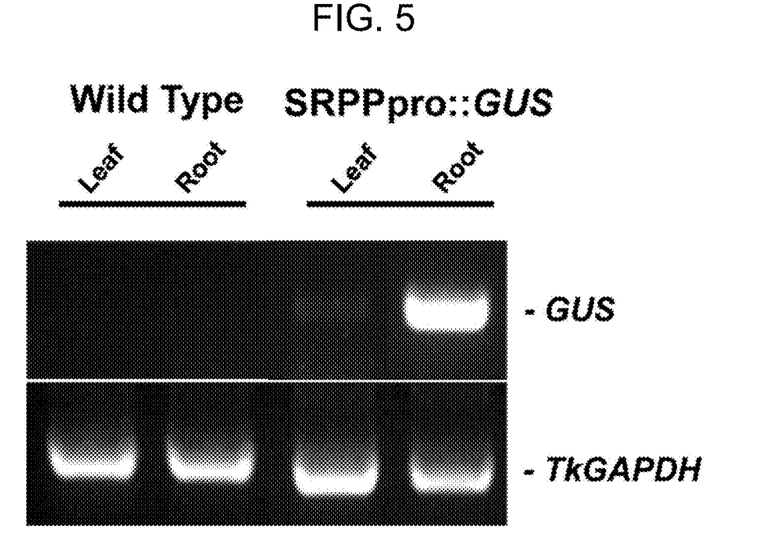
FIG. 5 includes RT-PCR results showing GUS gene expression in root tissues of non-transformed Russian dandelion (i.e., wild type) and in the roots and the leaf tissue of Russian dandelion transformed with SRPPpromoter::GUS.

GUS (i.e., marker gene) expression was clearly shown in the roots of SRPPpro::GUS transformant in which laticiferous tissues are present in a large amount. On the other hand, it was not shown in the leaves in which laticiferous tissues are hardly present (FIG. 5, right column) In the non-transformed wild type Russian dandelion (i.e., wild type), GUS gene expression was not detected in any tissues (FIG. 5, left column) TkGAPDH indicates a house-keeping gene. Those results indicate that the laticiferous tissue-specific expression of GUS gene is caused by the SRPP promoter.

Example 7

Tissue-Specific Expression of GUS Protein in Transformed Russian Dandelion

Figure 6:
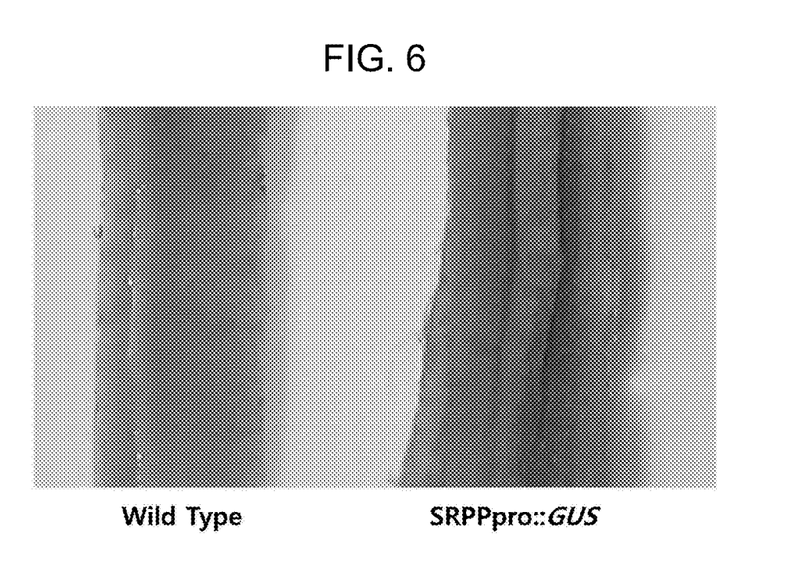
FIG. 6 includes photographs showing GUS staining results in the roots of the Russian dandelion SRPPpromoter::GUS transformant and in the root tissues of the non-transformed Russian dandelion (i.e., wild type).

In order to find out the tissues with expressed GUS proteins, the tissue specimen was immersed in a substrate solution for GUS staining (blue color). The histochemical GUS (beta-glucuronidase)-staining was performed according to a previously known method (Jefferson et al., 1987, Plant Mol. Biol. Rep. 5: 387-405). As shown in FIG. 6, blue GUS staining was clearly shown in the root tissues of SRPPpro::GUS transformant. However, in the root tissues of non-transformed wild type Russian dandelion, no such staining was shown.

Figure 7:
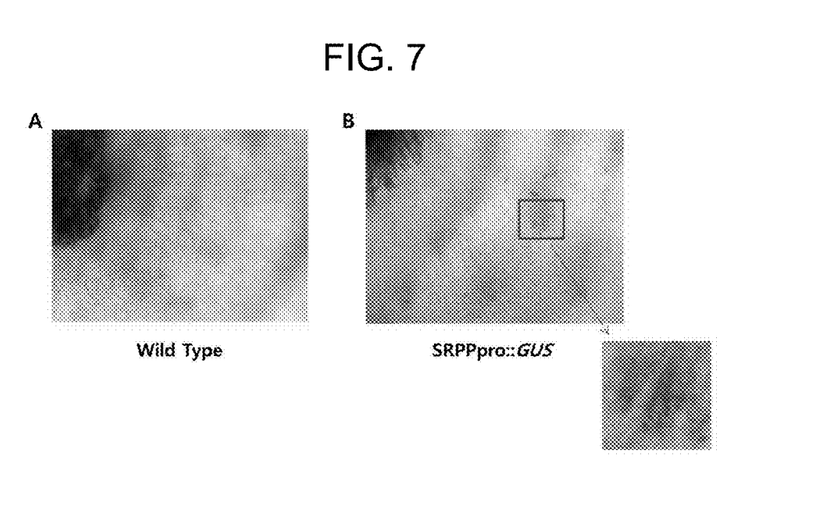
FIG. 7 includes photographs of the cross-section of the root tissues of a wild type Russian dandelion, and the cross-section of root tissues of the Russian dandelion SRPPpromoter::GUS transformant.

To see in greater detail whether or not the GUS staining in the roots of SRPPpro::GUS transformed Russian dandelion is tissue-specific, the roots were cut and the cross-section was observed under a microscope. The cross-section of the root tissues of the wild type Russian dandelion showed no GUS staining (FIG. 7, left column) However, the cross-section of the root tissues of the SRPPpro::GUS transformed Russian dandelion showed blue GUS staining only in laticiferous tissues (FIG. 7, right column) The area in the square was enlarged and additionally given below B.

Figure 8:
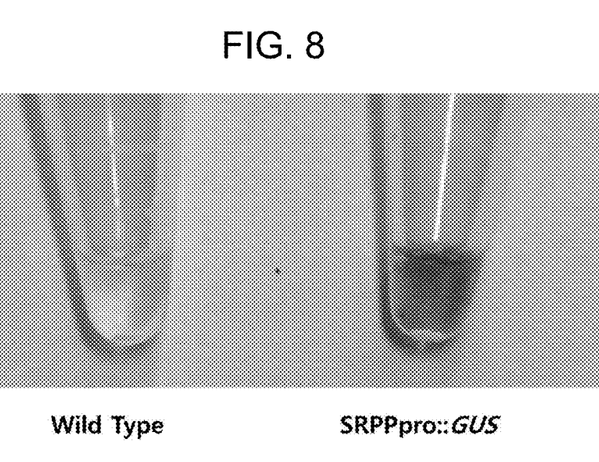
FIG. 8 illustrates results of examining GUS staining in laticiferous liquid produced from laticiferous tissue of the Russian dandelion SRPPpromoter::GUS transformant (right column) and the non-transformed Russian dandelion (i.e., wild type).

As a result of GUS staining in laticiferous liquid that has been produced from laticiferous root tissues, blue GUS staining was observed from the laticiferous liquid which is secreted from root latex tissues of the SRPPpro::GUS transformed Russian dandelion (FIG. 8, right column) On the other hand, no GUS staining was observed for laticiferous liquid from the roots of non-transformed Russian dandelion (i.e., wild type) (FIG. 8, left column) Those results indicate that the SRPP promoter is expressed in roots having a large amount of laticiferous tissue, in particular root laticiferous tissue, and in more accurate terms, from laticiferous liquid.

The invention claimed is:

1. An SRPP (small rubber particle-associated protein) promoter derived from a para rubber tree (*Hevea brasiliensis*), the promoter consisting of the nucleotide sequence of SEQ ID NO: 1, wherein said promoter is operably linked to a heterologous nucleic acid.

2. A recombinant plant expression vector comprising the promoter of claim 1.

3. The recombinant plant expression vector according to claim 2, in which the vector is constructed by operably linking a target heterologous nucleic acid to the SRPP promoter.

4. A plant transformed with the recombinant plant expression vector according to claim 2.

5. A transformed seed from a plant transformed with the recombinant plant expression vector, wherein said seed comprises said recombinant expression vector according to claim 2.

6. A method for laticiferous tissue-specific expression of a foreign gene in a transformed plant, the method comprising:
performing recombination of a foreign gene into the recombinant plant expression vector according to claim 2, and
transforming a plant with the recombinant plant expression vector.

7. The method according to claim 6, in which the foreign gene encodes a protein which is selected from a group consisting of a rubber polymerase, an enzyme relating to biosynthesis of rubber, interleukin, interferon, platelet-derived growth factor, human growth factor, human serum albumin, and erythropoietin.

8. The transformed plant according to claim 4, wherein the plant is a dicot plant.

9. The seed according to claim 5, wherein the plant is a dicot plant.

* * * * *